United States Patent
Tsai et al.

(10) Patent No.: US 10,357,297 B2
(45) Date of Patent: Jul. 23, 2019

(54) BIONIC FIXING APPARATUS

(71) Applicants: INDUSTRIAL TECHNOLOGY RESEARCH INSTITUTE, Hsinchu (TW); NATIONAL TAIWAN UNIVERSITY HOSPITAL, Taipei (TW)

(72) Inventors: Pei-Yi Tsai, Hsinchu (TW); Chih-Chieh Huang, Zhunan Township (TW); Yi-Hung Wen, Hsinchu (TW); Hsin-Hsin Shen, Zhudong Township (TW); Yi-Hung Lin, Zhubei (TW); De-Yau Lin, Tainan (TW); Jui-Sheng Sun, Taipei (TW); Chuan-Sheng Chuang, Taichung (TW); An-Li Chen, Tainan (TW); Ching-Chih Lin, Kaohsiung (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

( * ) Notice: Subject to any disclaimer, the term of this patent is extended or adjusted under 35 U.S.C. 154(b) by 782 days.

(21) Appl. No.: 14/554,521

(22) Filed: Nov. 26, 2014

(65) Prior Publication Data
US 2015/0150614 A1 Jun. 4, 2015

Related U.S. Application Data

(60) Provisional application No. 61/908,772, filed on Nov. 26, 2013.

(30) Foreign Application Priority Data

Jul. 2, 2014 (TW) .............................. 103122817 A

(51) Int. Cl.
*A61B 17/86* (2006.01)
*A61L 31/14* (2006.01)
*B33Y 80/00* (2015.01)

(52) U.S. Cl.
CPC ........ *A61B 17/8625* (2013.01); *A61B 17/864* (2013.01); *A61B 17/866* (2013.01);
(Continued)

(58) Field of Classification Search
CPC ............... A61L 2430/02; A61L 31/146; A61B 17/8625; A61B 17/86
See application file for complete search history.

(56) References Cited

U.S. PATENT DOCUMENTS 2,232,336 A 2/1941 Meersteiner et al.
2,913,031 A 11/1959 McKay et al.
(Continued)

FOREIGN PATENT DOCUMENTS

CN 1088423 A 6/1994
CN 1098281 A 2/1995
(Continued)

OTHER PUBLICATIONS

Chinese Office Action and Chinese Search Report, dated Jan. 17, 2017, for Chinese Application No. 201410406040.6.
(Continued)

*Primary Examiner* — David W Bates
(74) *Attorney, Agent, or Firm* — Birch, Stewart, Kolasch & Birch, LLP

(57) ABSTRACT

A bionic apparatus is provided. The bionic apparatus includes a flexible portion having a plurality of pores, a rigid portion connected with the flexible portion, and a supporting element disposed in the flexible portion. The pore size of each pore is between 50 μm to 500 μm. The flexible portion,
(Continued)

the rigid portion and the supporting element are one-piece formed by a additive manufacturing process.

9 Claims, 7 Drawing Sheets

(52) U.S. Cl.
CPC ............ *A61L 31/146* (2013.01); *B33Y 80/00* (2014.12); *A61L 2430/02* (2013.01)

(56) References Cited

U.S. PATENT DOCUMENTS

| | | | |
|---|---|---|---|
| 2,956,293 | A | 10/1960 | McKay et al. |
| 3,277,504 | A | 10/1966 | Smyth |
| 4,003,287 | A | 1/1977 | Ziaylek, Jr. |
| 4,636,121 | A | 1/1987 | Miller |
| 5,116,337 | A | 5/1992 | Johnson |
| 5,370,695 | A | 12/1994 | Meuli et al. |
| 5,876,434 | A | 3/1999 | Flomenblit et al. |
| 7,322,983 | B2 | 1/2008 | Harris |
| 8,388,660 | B1 | 3/2013 | Abdou |
| 8,535,357 | B2 * | 9/2013 | Stone .................. A61B 17/866 411/403 |
| 8,628,582 | B2 | 1/2014 | Lavi |
| 9,155,578 | B2 * | 10/2015 | Chegini ............... A61B 17/844 |
| 9,308,035 | B2 | 4/2016 | Biedermann et al. |
| 2002/0198527 | A1 * | 12/2002 | Muckter ............ A61B 17/1671 606/254 |
| 2004/0122431 | A1 * | 6/2004 | Biedermann ........ A61B 17/864 606/62 |
| 2004/0162560 | A1 | 8/2004 | Raynor et al. |
| 2004/0210217 | A1 | 10/2004 | Baynham et al. |
| 2005/0112397 | A1 | 5/2005 | Rolfe et al. |
| 2005/0143823 | A1 | 6/2005 | Boyd et al. |
| 2005/0192675 | A1 | 9/2005 | Robinson |
| 2006/0100630 | A1 | 5/2006 | West, Jr. |
| 2006/0106390 | A1 | 5/2006 | Jensen et al. |
| 2007/0038221 | A1 | 2/2007 | Fine et al. |
| 2007/0141110 | A1 | 6/2007 | Stone et al. |
| 2007/0265622 | A1 | 11/2007 | Aeschlimann et al. |
| 2009/0240289 | A1 | 9/2009 | Zipprich et al. |
| 2010/0042215 | A1 * | 2/2010 | Stalcup .................. A61B 17/68 623/16.11 |
| 2011/0123951 | A1 | 5/2011 | Lomicka |
| 2011/0166602 | A1 | 7/2011 | Malek |
| 2011/0213423 | A1 * | 9/2011 | Biedermann ...... A61B 17/8625 606/304 |
| 2011/0307073 | A1 | 12/2011 | Teoh et al. |
| 2012/0184993 | A1 * | 7/2012 | Arambula .......... A61B 17/7064 606/246 |
| 2012/0271362 | A1 * | 10/2012 | Martineau ............ A61B 17/863 606/304 |
| 2013/0030529 | A1 | 1/2013 | Hunt |
| 2013/0123862 | A1 | 5/2013 | Anderson et al. |
| 2014/0288649 | A1 * | 9/2014 | Hunt ....................... A61F 2/447 623/16.11 |
| 2015/0093717 | A1 | 4/2015 | Ali |
| 2015/0112342 | A1 | 4/2015 | Penzimer et al. |

FOREIGN PATENT DOCUMENTS

| | | |
|---|---|---|
| CN | 1204498 A | 1/1999 |
| CN | 1604759 A | 4/2005 |
| CN | 1891172 A | 1/2007 |
| CN | 2894638 Y | 5/2007 |
| CN | 101198291 A | 6/2008 |
| CN | 201082188 Y | 7/2008 |
| CN | 101317790 A | 12/2008 |
| CN | 201840550 U | 5/2011 |
| CN | 202682036 U | 1/2013 |
| CN | 202821579 U | 3/2013 |
| CN | 103167837 A | 6/2013 |
| EP | 1 112 722 A2 | 7/2001 |
| EP | 1 069 872 B1 | 5/2003 |
| EP | 1 762 189 A1 | 3/2007 |
| EP | 2400901 B1 | 5/2013 |
| TW | 330839 | 5/1998 |
| TW | 480169 B | 3/2002 |
| TW | 200416020 A | 9/2004 |
| TW | 200635565 A | 10/2006 |
| TW | 200708295 A | 3/2007 |
| TW | 200722036 A | 6/2007 |
| TW | I306396 B | 2/2009 |
| TW | 200936113 A | 9/2009 |
| TW | 200944176 A1 | 11/2009 |
| TW | 201100061 A | 1/2011 |
| TW | 201221108 A1 | 6/2012 |
| TW | 201235005 A1 | 9/2012 |
| TW | 201240653 A | 10/2012 |
| TW | 201249392 A1 | 12/2012 |
| TW | 201325577 A1 | 7/2013 |
| TW | 201325638 A1 | 7/2013 |
| TW | M458938 U | 8/2013 |
| WO | WO 2011/059995 A2 | 5/2011 |
| WO | WO 2012/024665 A2 | 2/2012 |
| WO | WO 2013/043218 A1 | 3/2013 |
| WO | WO 2013/043432 A1 | 3/2013 |

OTHER PUBLICATIONS

Taiwanese Office Action and Taiwanese Search Report, dated Feb. 18, 2017, for Taiwanese Application No. 104140981.
Achour et al. "Stress distribution in dental implant with elastomeric stress barrier", Materials and Design, 32, (2011), pp. 282-290.
Breguet et al. "Compact, Light Weight Mechanisms for High Precision Micro-Manipulators".
Chen et al. "Pullout strength for cannulated pedicle screws with bone cement augmentation in severely osteoporotic bone: Influences of radial hole and pilot hole tapping", Clinical Biomechanics, 24, (2009), pp. 613-618.
Emmelmann et al. "Laser freeform fabrication of porous network structures for dental application", Proceedings fo the Fifth International WLT-Conference on Lasers in Manufacturing, Munich, Jun. 2009, pp. 453-457.
Frost & Sullivan, 2012 United States Medical Devices Outlook "Setting the Stage for What is Next", Jul. 2012, NB3E-54.
Jory D. Richman, MD "Odontoid Screw Fixation for Type II Odontoid Fractures", Operative Techniques in Orthopaedics, vol. 8, No. 1 Jan. 1998: pp. 16-21.
Kissel et al. "Comparison of Pullout Strength of Small-Diameter Cannulated and Solid-Core Screws", The Journal of Foot & Ankle Surgery, 42(6): 334-338.
Lin et al. "A biomechanical study of the cortex-anchorage vertebral screw", Clinical Biomechanics, 18, (2003), S25-S32.
Liu et al. "Design and biomechanical study of a modified pedicle screw", Chinese Journal of Traumatology, 2010; 13(4): 222-228.
Migliorati et al. "Miniscrew design and bone characteristics: An experimental study of primary stability", American Journal of Orthodontics and Dentofacial Orthopedics, Aug. 2012, vol. 142, Issue 2, pp. 228-234.
Mikos et al. "Laminated three-dimensional biodegradable foams for use in tissue engineering", Biomaterials 1993, vol. 14, No. 5, pp. 323-330.
Shen et al. "Hollow-Bone-Graft Dynamic Hip Screw Can Fix and Promote Bone Union after Femoral Neck Fracture: an Experimental Research", International Journal of Medical Sciences, 2012; 9(10):916-922. doi: 10.7150 / ijms.4567.
Sumner et al. "Functional adaptation and ingrowth of bone vary as a function of hip implant stiffness", Journal of Biomechanics, 31, (1998), pp. 909-917.
Taiwanese Office Action and Search Report for Taiwanese Application No. 103118970, dated Feb. 15, 2016.
Taiwanese Office Action and Search Report for Taiwanese Application No. 103122519, dated Dec. 2, 2015.
Taiwanese Office Action and Search Report for Taiwanese Application No. 103122817, dated Nov. 26, 2015.

(56) References Cited

OTHER PUBLICATIONS

U.S. Office Action for U.S. Appl. No. 14/555,251, dated Dec. 4, 2017.
U.S. Office Action for U.S. Appl. No. 14/977,234, dated Dec. 26, 2017.
U.S. Office Action for U.S. Appl. No. 14/555,251, dated May 25, 2018.
U.S. Office Action for U.S. Appl. No. 14/555,251, dated Sep. 7, 2018.

* cited by examiner

BIONIC FIXING APPARATUS

CROSS-REFERENCE TO RELATED APPLICATION

This application claims the benefits of U.S. provisional application 61/908,772, filed Nov. 26, 2013, and Taiwan application Serial No. 103122817, filed Jul. 2, 2014, the disclosures of which are incorporated by reference herein in its entirety

TECHNICAL FIELD

The technical field relates to a bionic fixing apparatus.

BACKGROUND

With the advances in technology and medicine, implants, such as bone screws, are used to fix the biological tissue in the human body for medical purpose, for example, for repairing accidental injury or nature aging. However, modulus of elasticity of the conventional implants is much higher than that of the biological tissue in the human body. When the force applied to the human body is too high, the biological tissue tends to necrosis or wear, and the implants may also be loosened.

In general, pores are disposed on the implants, such as bone screws to lower the modulus of elasticity. However, the conventional process of manufacturing implants includes a special sintering process or a surface coating process, and then executing a pore-opening by laser. Positions of the pores generated by such method may not be fixed, the pores are not connected to each other, and formed only on the surface of the implants, such that the porosity of the pores may be uncertain. Besides, it may be hard to form pores with regular shape by the conventional process. If the pores are too large, then lack of rigidity may generate problems such as implants loosening or breaking after implantation of bone healing or long-term use. On the contrary, if the pores are too small, then problems that the biological tissue tends to necrosis and wear mentioned above may not be solved.

SUMMARY

The disclosure is directed to a bionic fixing apparatus having flexible portion with a plurality of pores. Various micro-structures may be generated on the implants by an additive manufacturing (AM) method. Modulus of elasticity of the implants may be effectively decreased by the micro-structures, and the pore size between 50 and 500 μm may enhance the proliferation and combination of the biological tissue.

According to one embodiment, a bionic apparatus including a flexible portion, a rigid portion and a supporting portion is provided. The flexible portion has a plurality of pores, and a pore size of each pore is between 50 to 500 μm.

DETAILED DESCRIPTION

Figure 1:
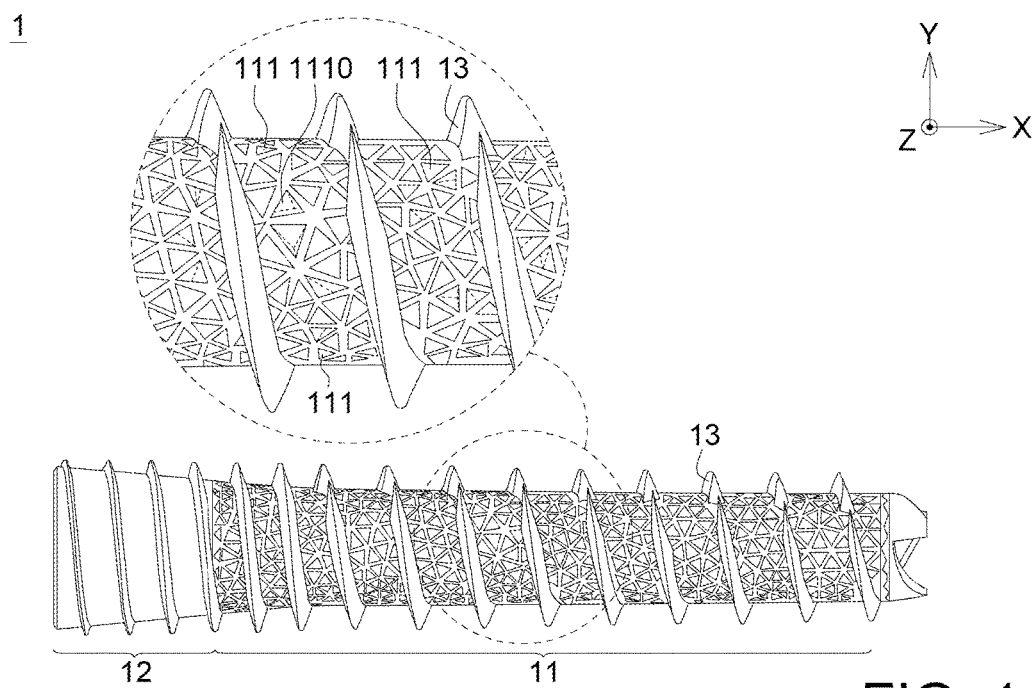
FIG. 1 illustrates the bionic fixing apparatus in the first embodiment according to the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The bionic apparatus in one embodiment according to the disclosure includes a flexible portion having a plurality of pores. The pore size of each pore is between 50 μm to 500 μm, and the pores are formed by stacking multi-dimensional lines and planes or curved surfaces. Besides, the bionic apparatus may also include a rigid portion connected with the flexible portion, and the rigid portion and the flexible portion are one-piece formed in some embodiments.

The following describes the bionic fixing apparatus according to the disclosure in the first to fourth embodiments in cooperation with FIG. 1 to FIG. 4. In these embodiments, although the pores have different shapes and arrangements, the pore size of each pore is between 50 μm and 200 μm. Here, the pore size is defined as the largest width of the pore. Further, the porosity of the bionic fixing apparatus is between 0.17 and 0.36 in the first to fourth embodiments.

First Embodiment

FIG. 1 illustrates the bionic fixing apparatus 1 in the first embodiment according to the disclosure. The bionic fixing apparatus 1 includes a flexible portion 11 having a plurality of pores 111. In this embodiment, the plurality of the pores 111 is irregularly arranged, and formed by stacking multi-dimensional lines and planes 1110. Each pore is triangular, and the pore sizes of the pores 111 (the largest width of the pores 111) are not completely the same. Besides, the porosity of the bionic fixing apparatus 1 in the first embodiment of the disclosure is 0.34.

In this embodiment, the bionic apparatus 1 may include a rigid portion 12 connected with the flexible portion 11, and the rigid portion 12 and the flexible portion 11 are one-piece"

formed. The difference between the rigid portion 12 and the flexible portion 11 is that the rigid portion 12 may not have pores 111.

Further, the bionic fixing apparatus 1 may also include a thread portion 13 surrounding the flexible portion 11 and the rigid portion 12. The thread portion 13, the flexible portion 11 and the rigid portion 12 are one-piece formed. In one embodiment, the thread portion 13 may make the bionic fixing apparatus 1 easily to be implanted and fixed into the organism.

Second Embodiment

Figure 2:
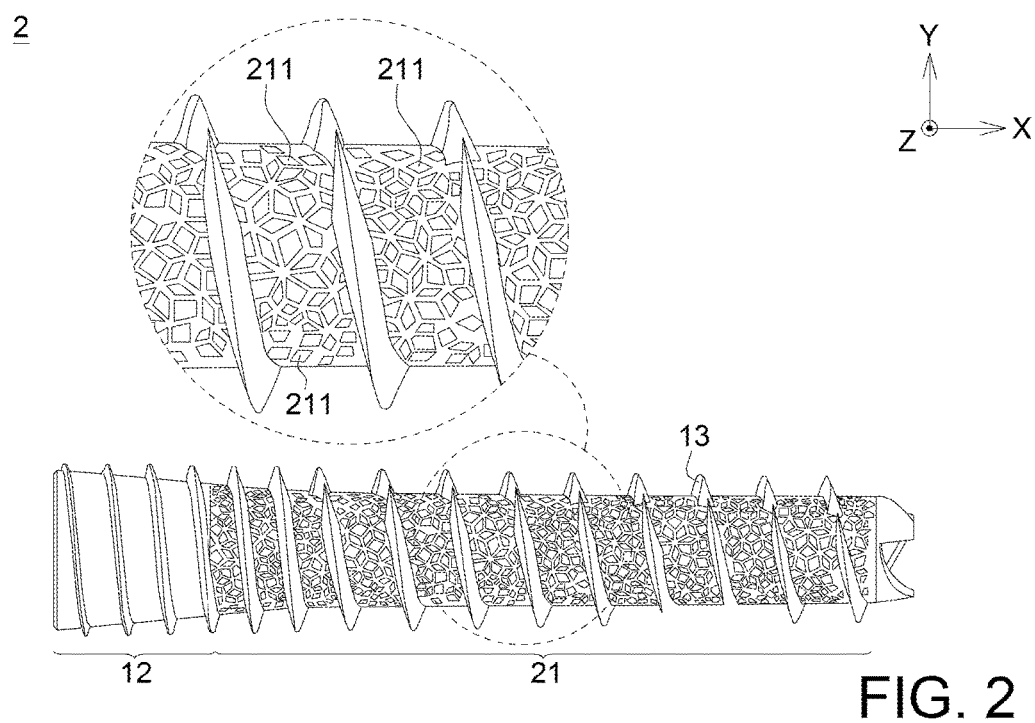
FIG. 2 illustrates the bionic fixing apparatus in the second embodiment according to the disclosure.

FIG. 2 illustrates the bionic fixing apparatus 2 in the second embodiment according to the disclosure. Similar to the first embodiment, the bionic fixing apparatus 2 includes a flexible portion 21 having a plurality of pores 211. In this embodiment, the plurality of the pores 211 is irregularly arranged, each pore is quadrilateral, and the pore sizes of the pores 211 (the largest width of the pores 211) are not completely the same. It should be noted that "quadrilateral" here is not limited to a parallelogram or trapezoid. Instead, the pores 211 may include rectangular pores, diamond-shaped pores and irregular quadrilateral pores, etc., or the combination of the quadrilateral pores above. Besides, the porosity of the bionic fixing apparatus 2 in the second embodiment of the disclosure is 0.32.

Similarly, the bionic apparatus 2 may include a rigid portion 12 and a thread portion 13. The rigid portion 12, the thread portion 13 and the flexible portion 21 are one-piece formed, and the detailed description is omitted here.

Third Embodiment

Figure 3:
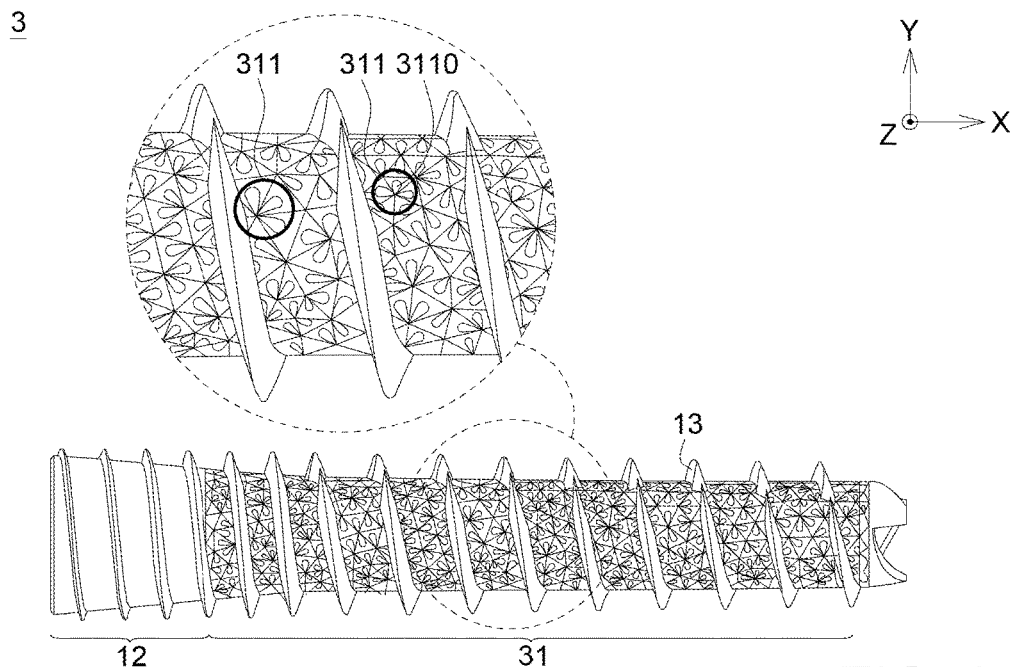
FIG. 3 illustrates the bionic fixing apparatus in the third embodiment according to the disclosure.

FIG. 3 illustrates the bionic fixing apparatus 3 in the third embodiment according to the disclosure. The bionic fixing apparatus 3 includes a flexible portion 31 having a plurality of pores 311. In this embodiment, the plurality of the pores 311 is irregularly arranged, and formed by stacking multi-dimensional lines and curved surfaces 3110. Each pore is blade-shaped or radial, and the pore sizes of the pores 311 (the largest width of the pores 311) are not completely the same. Besides, the porosity of the bionic fixing apparatus 3 in the third embodiment of the disclosure is 0.17.

Similarly, the bionic apparatus 3 may include a rigid portion 12 and a thread portion 13. The rigid portion 12, the thread portion 13 and the flexible portion 31 are one-piece formed.

Fourth Embodiment

Figure 4:
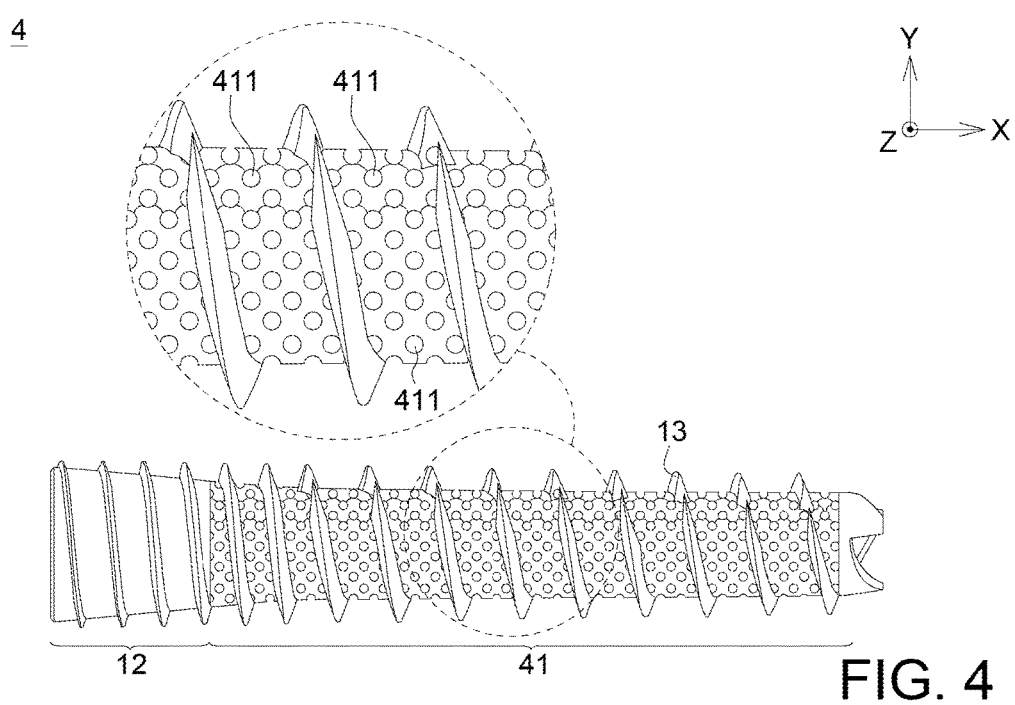
FIG. 4 illustrates the bionic fixing apparatus in the fourth embodiment according to the disclosure.

FIG. 4 illustrates the bionic fixing apparatus 4 in the fourth embodiment according to the disclosure. The bionic fixing apparatus 4 includes a flexible portion 41 having a plurality of pores 411. The difference between the fourth embodiment and the first to third embodiments is that the plurality of the pores 411 is regularly arranged in this embodiment. Each pore is circular, and the pore sizes of the pores 411 (the diameter of the pores 411) are the same. Besides, the porosity of the bionic fixing apparatus 4 in the fourth embodiment of the disclosure is 0.36.

Similarly, the bionic apparatus 4 may include a rigid portion 12 and a thread portion 13. The rigid portion 12, the thread portion 13 and the flexible portion 41 are one-piece formed.

TABLE 1 shows the result of the 3-point bending test executed on the bionic apparatuses in the first to fourth embodiments according to the disclosure. 3-point bending test is mainly to achieve the greatest damage strength which the bionic fixing apparatus can withstand by static mechanical properties of 3-point bending test at the time that the destruction is generated. Before the test, the loading device is placed on the top center of the bionic fixing apparatus, and then a force of 5 N is applied downwardly on the bionic fixing apparatus, followed by applying force with loading speed of 0.05 mm/s until the bionic fixing apparatus causes damage or the loading is dropped below to 30% of the maximum loading. Each bionic fixing apparatus is tested five groups, and the loading-displacement curve is mapped by data arising from the test, and the maximum loading value is recorded.

TABLE 1

|  | First Embodiment | Second Embodiment | Third Embodiment | Fourth Embodiment |
| --- | --- | --- | --- | --- |
| Porosity | 0.34 | 0.32 | 0.17 | 0.36 |
| Strength which the bionic fixing apparatus can withstand (N) | 288 | 85 | 458.7 | 378 |
| Maximum stress which the bionic fixing apparatus can withstand on the surface (MPa) | 5015 | 1480 | 7987 | 6582 |

Then, the following describes the bionic fixing apparatus according to the disclosure in the fifth to eighth embodiments in cooperation with FIG. 5 to FIG. 8. In these embodiments, although the pores have different shapes and arrangements, the pore size of each pore is between 300 and 500 μm. Here, the pore size is defined as the largest width of the pore. Further, the porosity of the bionic fixing apparatus is between 0.31 and 0.55 in the fifth to eighth embodiments.

Fifth Embodiment

Figure 5:
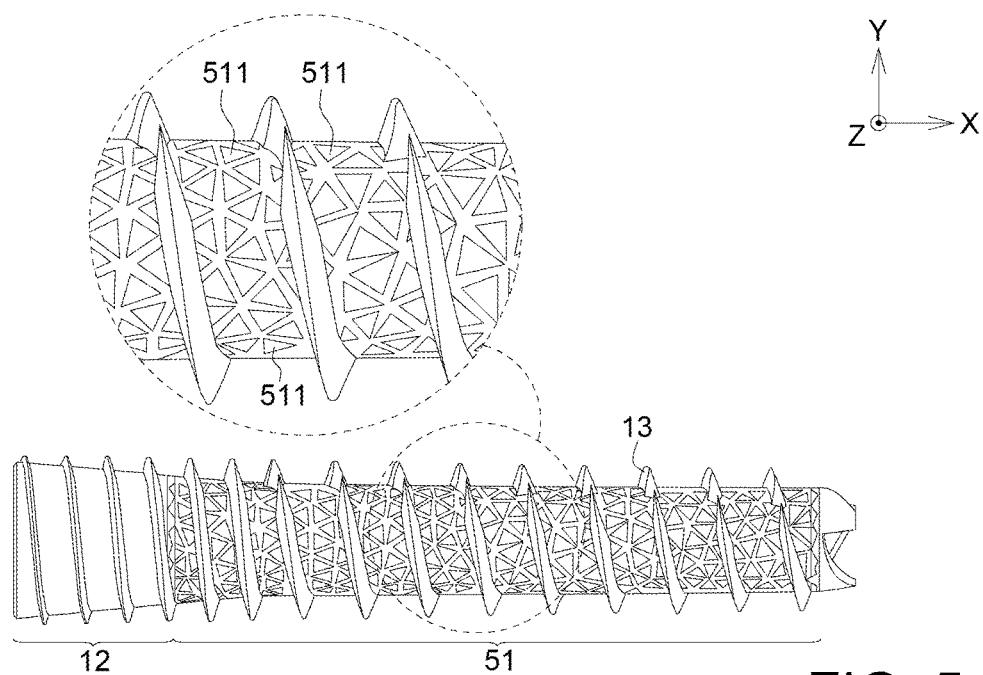
FIG. 5 illustrates the bionic fixing apparatus in the fifth embodiment according to the disclosure.

FIG. 5 illustrates the bionic fixing apparatus 5 in the fifth embodiment according to the disclosure. Similar to the first embodiment, the bionic fixing apparatus 5 includes a flexible portion 51 having a plurality of pores 511. In this embodiment, the plurality of the pores 511 is irregularly arranged. Each pore is triangular, and the pore sizes of the pores 511 (the largest width of the pores 511) are not completely the same. Besides, the porosity of the bionic fixing apparatus 5 in the fifth embodiment of the disclosure is 0.34.

Similarly to the first embodiment, the bionic apparatus 5 may include a rigid portion 12 and a thread portion 13. The rigid portion 12, the thread portion 13 and the flexible portion 51 are one-piece formed.

Sixth Embodiment

Figure 6:
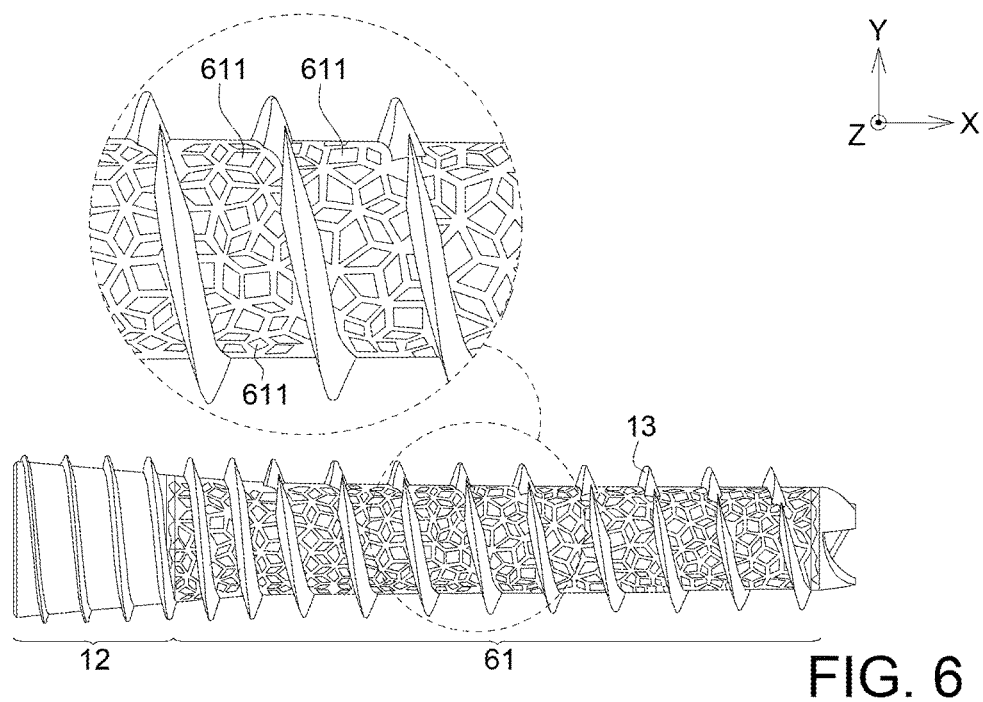
FIG. 6 illustrates the bionic fixing apparatus in the sixth embodiment according to the disclosure.

FIG. 6 illustrates the bionic fixing apparatus 6 in the sixth embodiment according to the disclosure. Similar to the second embodiment, the bionic fixing apparatus 6 includes a flexible portion 61 having a plurality of pores 611. In this embodiment, the plurality of the pores 611 is irregularly arranged, each pore is quadrilateral, and the pore sizes of the pores 611 (the largest width of the pores 611) are not completely the same. It should be noted that "quadrilateral" here is not limited to a parallelogram or trapezoid. Instead, the pores 611 may include rectangular pores, diamond-shaped pores and irregular quadrilateral pores, etc., or the combination of the quadrilateral pores above. Besides, the porosity of the bionic fixing apparatus 6 in the sixth embodiment of the disclosure is 0.31.

Similarly to the second embodiment, the bionic apparatus 6 may include a rigid portion 12 and a thread portion 13. The rigid portion 12, the thread portion 13 and the flexible portion 61 are one-piece formed.

Seventh Embodiment

Figure 7:
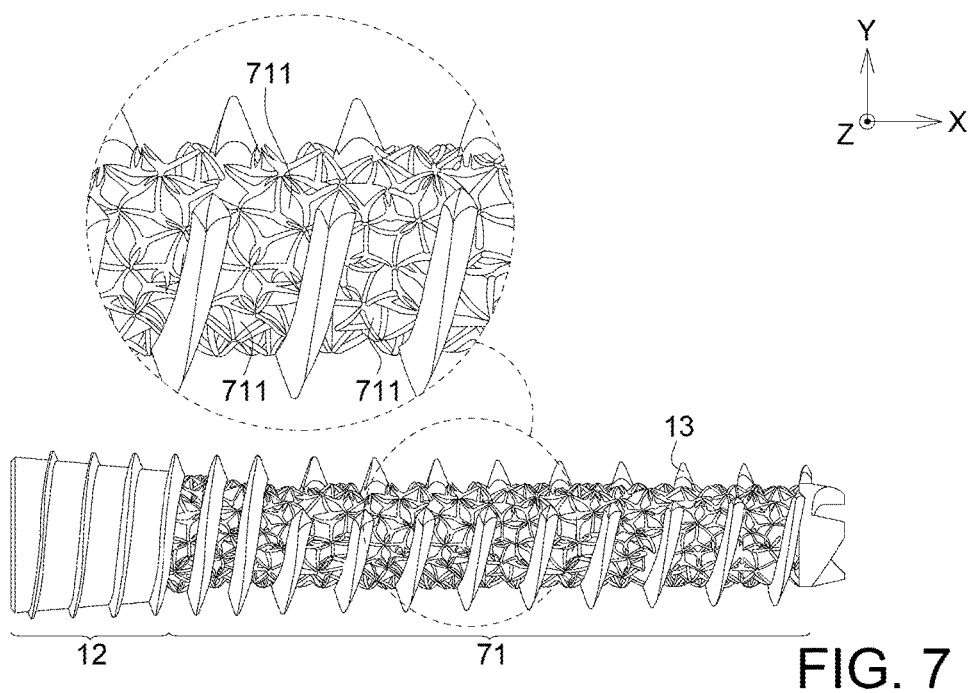
FIG. 7 illustrates the bionic fixing apparatus in the seventh embodiment according to the disclosure.

FIG. 7 illustrates the bionic fixing apparatus 7 in the seventh embodiment according to the disclosure. The bionic fixing apparatus 7 includes a flexible portion 71 having a plurality of pores 711. The plurality of the pores 711 is irregularly arranged, and the pore sizes of the pores 711 (the largest width of the pores 711) are not completely the same. In this embodiment, the pores 711 are such as triangular, quadrilateral, polygonal, other irregular shaped or the combination above. Besides, the porosity of the bionic fixing apparatus 7 in the seventh embodiment of the disclosure is 0.55.

Similarly to the first embodiment, the bionic apparatus 7 may include a rigid portion 12 and a thread portion 13. The rigid portion 12, the thread portion 13 and the flexible portion 71 are one-piece formed.

Eighth Embodiment

Figure 8:
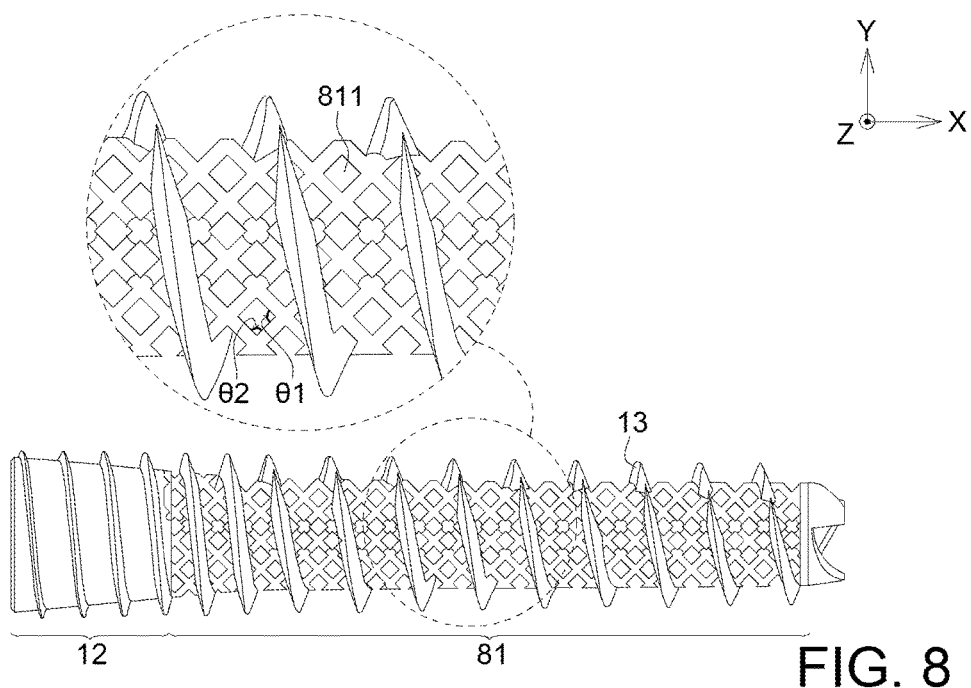
FIG. 8 illustrates the bionic fixing apparatus in the eighth embodiment according to the disclosure.

FIG. 8 illustrates the bionic fixing apparatus 8 in the eighth embodiment according to the disclosure. The bionic fixing apparatus 8 includes a flexible portion 81 having a plurality of pores 811. The difference between the eighth embodiment and the fifth to seventh embodiment is that the plurality of the pores 811 is regularly arranged.

In this embodiment, the flexible portion 81 may include a grid array structure, and the pores 811 are a plurality of meshes. As shown in FIG. 8, each mesh of the grid array structure has a first included angle $\theta 1$ and a second included angle $\theta 2$. The first included angle $\theta 1$ is arranged along a force-receiving direction of the bionic fixing apparatus 8, for example, arranged along X direction in the embodiment. The second included angle $\theta 2$ is arranged along a direction perpendicular to the force-receiving direction of the bionic fixing apparatus 8, for example, arranged along Y direction in the embodiment. Besides, the second included angle $\theta 2$ is smaller than 90 degrees. The pores 811 may be diamond-shaped, and the pore sizes are the same. The porosity of the bionic fixing apparatus 8 in the eighth embodiment of the disclosure is 0.47.

In one embodiment, the second included angle $\theta 2$ may be 40 degrees, and the porosity may be 0.52. Assumed that a compressive test is applied to the grid array structure, the compressive strength may be increased to 1931.2 kg and a displacement of approximately 3.6207 mm may be generated.

Similarly, the bionic apparatus 8 may include a rigid portion 12 and a thread portion 13. The rigid portion 12, the thread portion 13 and the flexible portion 81 are one-piece formed.

Figure 9:
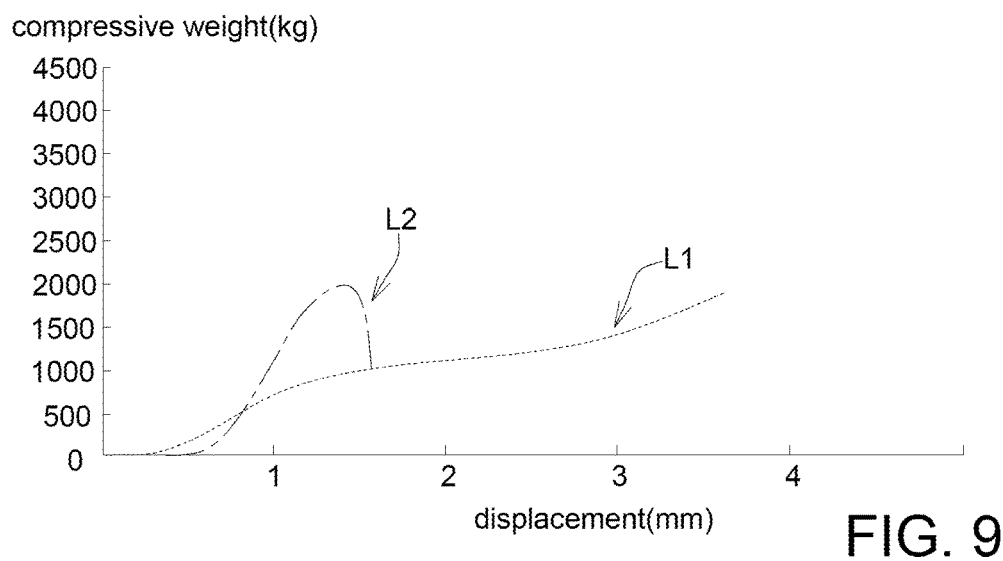
FIG. 9 illustrates the compressive weight versus the displacement from the result of the compressive test executed on the bionic apparatus in the eighth embodiment of the disclosure and a bionic fixing apparatus according to a first comparative example.

FIG. 9 illustrates the compressive weight versus the displacement from the result of the compressive test executed on the bionic apparatus 8 in the eighth embodiment of the disclosure and a bionic fixing apparatus according to a first comparative example. In this test, the difference between the bionic fixing apparatus according to the first comparative example and the bionic apparatus 8 in the eighth embodiment of the disclosure is that the second included angle $\theta 2$ of the first comparative example is larger than 90 degrees. Besides, the curve L1 corresponds to the bionic apparatus 8 in the eighth embodiment of the disclosure, and the curve L2 corresponds to the bionic fixing apparatus according to the first comparative example.

As shown in FIG. 9, since the bionic fixing apparatus according to the first comparative example (shown by curve L2) has the second included angle $\theta 2$ larger than 90 degrees, the modulus of elasticity is higher, such that the displacement is not easily generated. But when the compressive weight is increased to about 2000 kg, the bionic fixing apparatus according to the first comparative example is broken. Instead, since the bionic fixing apparatus 8 in the eighth embodiment according to the disclosure (shown by curve L1) has the second included angle $\theta 2$ smaller than 90 degrees, the modulus of elasticity is lower, such that the displacement may be easily generated. But when the compressive weight is increased to about 2000 kg, the bionic fixing apparatus 8 in the eighth embodiment according to the disclosure may not be broken.

Therefore, since the bionic fixing apparatus 8 in the eighth embodiment according to the disclosure has the second included angle $\theta 2$ smaller than 90 degrees, the modulus of elasticity is lower, and the safety may be increased when using the bionic fixing apparatus 8 in such as implanting into the organism.

TABLE 2 shows the result of the 3-point bending test executed on the bionic apparatuses in the fifth to eighth embodiments according to the disclosure.

TABLE 2

| | Fifth Embodiment | Sixth Embodiment | Seventh Embodiment | Eighth Embodiment |
|---|---|---|---|---|
| Porosity | 0.34 | 0.31 | 0.55 | 0.47 |
| Strength which the bionic fixing apparatus can withstand (N) | 215 | 227 | 107 | 78 |
| Maximum stress which the bionic fixing apparatus can withstand on the surface (MPa) | 3743 | 3952 | 1863 | 1358 |

According to the results shown in TABLE 1 and TABLE 2, the bionic fixing apparatuses in the embodiments according to the disclosure may have different mechanism strengths because of the different shapes and the arrangements of the pores. But generally speaking, the bionic fixing apparatus having pores with smaller pore size (such as the first to fourth embodiments having pore size between 50 and 200 μm) may have larger mechanism strengths than the bionic fixing apparatus having pores with larger pore size (such as the fifth to eighth embodiments having pore size between 300 and 500 μm).

However, although the bionic fixing apparatus having pores with larger pore size may have smaller mechanism strengths, the bionic fixing apparatus having pores with larger pore size may provide better physiological microenvironment. That is, when the bionic fixing apparatus having pores with larger pore size is implanted into the organism, cells or tissues in the organism may be more easily moved therein, and the repair of the tissues may be accelerated.

Therefore, the bionic fixing apparatuses in the ninth, tenth, and eleventh embodiments according to the disclosure are introduced for increasing the mechanism strengths of the bionic fixing apparatus having pores with larger pore size.

Ninth Embodiment to Eleventh Embodiment

Figure 10A:
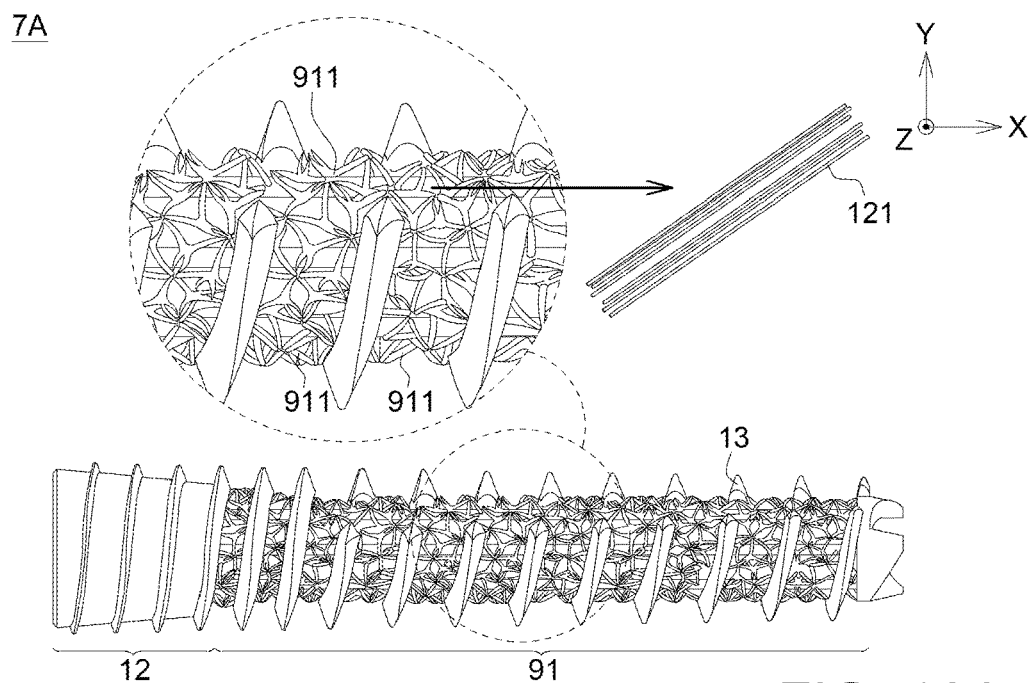
FIG. 10A illustrates the bionic fixing apparatus in the ninth embodiment according to the disclosure.

FIG. 10A illustrates the bionic fixing apparatus 7A in the ninth embodiment according to the disclosure. The bionic fixing apparatus 7A may include a flexible portion 91 having a plurality of pores 911 similar to the bionic fixing apparatus 7 in the seventh embodiment. The plurality of the pores 911 is irregularly arranged, and the pore sizes of the pores 911 (the largest width of the pores 911) are not completely the same.

It is different from the bionic fixing apparatus 7 in the seventh embodiment that the bionic apparatus 7A may further include a supporting element 121 disposed in the flexible portion 91, and the supporting element 121 and the flexible portion 91 are one-piece formed. In this embodiment, the supporting element 121 includes a strip structure.

Similarly, the bionic apparatus 7A may include a rigid portion 12 and a thread portion 13. The rigid portion 12, the thread portion 13 and the flexible portion 91 are one-piece formed.

Figure 10B:
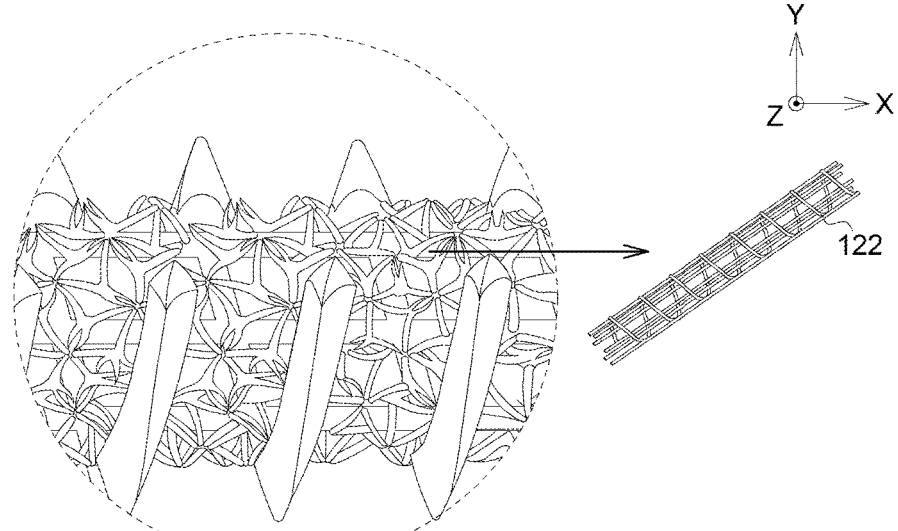
FIG. 10B and FIG. 10C illustrate enlarged portion of the bionic fixing apparatuses in the tenth embodiment and eleventh embodiment according to the disclosure respectively.
Figure 10C:
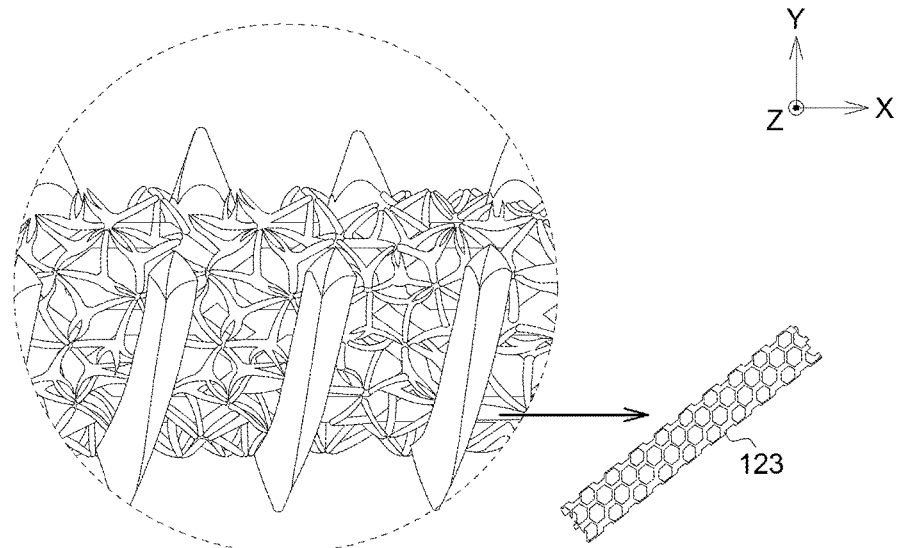

FIG. 10B and FIG. 10C illustrate enlarged portion of the bionic fixing apparatuses 7B and 7C in the tenth embodiment and eleventh embodiment according to the disclosure respectively. Similarly, the bionic fixing apparatuses 7B and 7C may include the structure similar to the structure of the bionic fixing apparatus 7 in the seventh embodiment.

Besides, it is different from the bionic fixing apparatus 7A in the ninth embodiment about the structure of the supporting element. As shown in FIG. 10B and FIG. 10C, the supporting element 122 in the tenth embodiment and the supporting element 123 in the eleventh embodiment may include a mesh structure or a combination of the strip structure and the mesh structure.

In the ninth embodiment to the eleventh embodiment, the supporting elements 121, 122 and 123 are formed to enhance the mechanism of the bionic fixing apparatuses 7A, 7B and 7C. TABLE 3 shows the result of the 3-point bending test executed on the bionic apparatuses in the ninth to eleventh embodiments according to the disclosure.

TABLE 3

|  | Ninth Embodiment | Tenth Embodiment | Eleventh Embodiment |
|---|---|---|---|
| Porosity | 0.46 | 0.44 | 0.43 |
| Strength which the bionic fixing apparatus can withstand (N) | 482.58 | 375.85 | 553.21 |
| Maximum stress which the bionic fixing apparatus can withstand on the surface (MPa) | 8403 | 6544 | 9633 |

According to the result shown in TABLE 3, the bionic apparatuses 7A, 7B and 7C in the ninth to eleventh embodiments according to the disclosure may have obviously improved mechanism strengths compared with the bionic apparatus 7 in the seventh embodiment. For example, the strengths which the bionic fixing apparatuses 7A, 7B and 7C in the ninth to eleventh embodiments can withstand are three times over the strength which the bionic fixing apparatus 7 in the seventh embodiment can withstand.

It should be noted that even the supporting elements are added in the bionic fixing apparatus 7 in the ninth to eleventh embodiments as examples, however, the disclosure is not limited thereto. The supporting element may be added to other embodiments according to the disclosure for enhancing the mechanism strengths of these bionic fixing apparatuses. That is, the mechanism strengths of the bionic fixing apparatus having pores with larger pore size (such as between 300 and 500 μm) may be enhanced by the supporting element including a strip structure, a mesh structure or a combination of the strip structure and the mesh structure, and the bionic fixing apparatus having pores with larger pore size may also maintain providing better physiological microenvironment.

In addition, the complex micro-structure in the embodiments mentioned above may be manufactured by an additive manufacturing (AM) process. The flexible portion, the rigid portion, and the thread portion are all one-piece formed. Further, various sized, shapes and arrangements of the pores according to the embodiments of the disclosure may be easily completed by the additive manufacturing process. On the contrary, the conventional process (including a special sintering process or a surface coating process to the implants, and then executing a surface treatment by laser to enhance bone integration) is not only more complex, but also needs more manufacturing cost, which is not suitable to manufacture the structures in the embodiments of the disclosure.

The additive manufacturing process may also be known as rapid prototyping (RP), rapid manufacturing (RM) or 3D Printing. It is rectified as additive manufacturing process by American Society for Testing and Materials (ASTM) in 2009. Researchers have divided the additive manufacturing process into seven types as show in TABLE 4. The seven types include: Vat Photopolymerization, Material Jetting, Binder Jetting, Material Extrusion, Powder Bed Fusion, Sheet Lamination, and Directed Energy Deposition.

TABLE 4

| Process | Material | Application |
|---|---|---|
| Vat Photo-polymerization | photopolymers | Prototyping |
| Material Jetting | polymers, waxes | Prototyping |
| Binder Jetting | polymers, metals | Casting Pattern |
| Material Extrusion | foundry sand | Prototyping, Casting Molds, Direct Part |
| Powder Bed Fusion | polymers | Prototyping |
| Sheet Lamination | polymers, metals | Prototyping, Direct Part |
| Directed Energy Deposition | paper, metals | Prototyping, Direct Part |

The characteristics of the additive manufacturing process are that the three-dimensional (3D) image is transferred to two-dimensional (2D) cross-sections, and products can be made layer by layer according to the two-dimensional cross-sections, to form a three-dimensional object. Compared with the conventional process, the additive manufacturing process may avoid wasting materials, and be more suitable for application of highly complicated structure, customized, and small or medium amount of production.

During the manufacturing process of the bionic fixing apparatus according to the embodiments of the disclosure, the 3D digital model of the bionic fixing apparatus is transferred to a 2D cross-section having thickness between 20-50 μm. And a feeding system will spread out a 20-50 μm thickness layer of powder materials (such as metals, alloys, ceramics or polymeric biomaterials) with particle size smaller than 25 μm in a low-oxygen atmosphere (concentration of $O_2$ is smaller than 10,000 ppm).

Then, the fiber laser beam (with wavelength 1070 nm) is focused to the laminated area (50-150 μm) by the scanning galvanometer. The focused beam is moved corresponding to the 2D cross-sections (the moving speed is 500-1500 mm/s), such that the powder materials is heating up above their melting point to adding a layer of structure. By repeating this procedure, the 3D bionic fixing apparatus can be made layer by layer according to the 2D cross-sections. The additive manufacturing process may produce the highly complicated shapes, inner flow channels, and inner structures which are difficult to make by the conventional process.

In the embodiments of the disclosure, a material of the bionic fixing apparatus may include metals, alloys, ceramics or polymeric biomaterials. In some embodiments, the bionic fixing apparatus may be a hollow structure. The hollow structure may correspond to the pores of the flexible portion to produce an atmosphere which is more suitable for cells or tissues of aquatic organisms growing. Besides, although the thread portion 13 surrounding the rigid portion 12 and the flexible portion are illustrated in each embodiment mentioned above, the disclosure is not limited thereto. In some embodiments, the bionic fixing apparatus may not include the rigid portion 12 and the thread portion 13.

The bionic fixing apparatus according to the embodiments of the disclosure may be applied to fix different parts of the organism. For example, the bionic fixing apparatus may be applied to an artificial tooth root, vertebral screws, artificial discs, intramedullary nails or screws. Since the bionic fixing apparatus may be manufactured by the additive manufacturing process, it is easy to design different structures to correspond to different parts of the organism.

The following describes using the bionic fixing apparatus in the embodiment of the disclosure (as experimental groups) and the commercially available bionic fixing apparatus (as a control group) to proceed with an animal experiment. In this animal experiment, the bionic fixing apparatuses are used as bone screws, and the New Zealand white rabbit is used as an experimental subject. 500 mg/kg ketamine is used as an anesthetic.

The experiment has five groups: the control group is the commercially available bionic fixing apparatus; the first experimental group is a bionic fixing apparatus having a plurality of pores along a single direction; the second experimental group is the bionic fixing apparatus in the first experimental group adding growth factor BMP-2; the third experimental group is the bionic fixing apparatus in the first embodiment according to the disclosure; the fourth experimental group is the bionic fixing apparatus in the first embodiment according to the disclosure adding growth factor BMP-2. The apparatuses in these five groups are implanted into femoral joints of the rabbits respectively in the experiment. After six weeks and twelve weeks, the rabbits are sacrificed by overdosed anesthesia and immersed in formalin. Then, the biocompatibility observation and mechanical tests are executed.

According to the result of the biocompatibility observation, relatively dense new bone tissues may be seen near the pores of the bionic fixing apparatus in the first to fourth experimental groups compared to the control group. Besides, the new bone tissues are more obvious in the third and fourth experimental groups than in the first and second experimental groups. This result shows that the bionic fixing apparatus in the embodiment of the disclosure has better biocompatibility, and the bone cells may grow therein more easily. According to the result of measuring the bone volume, the more obvious evidence may be shown.

Figure 11:
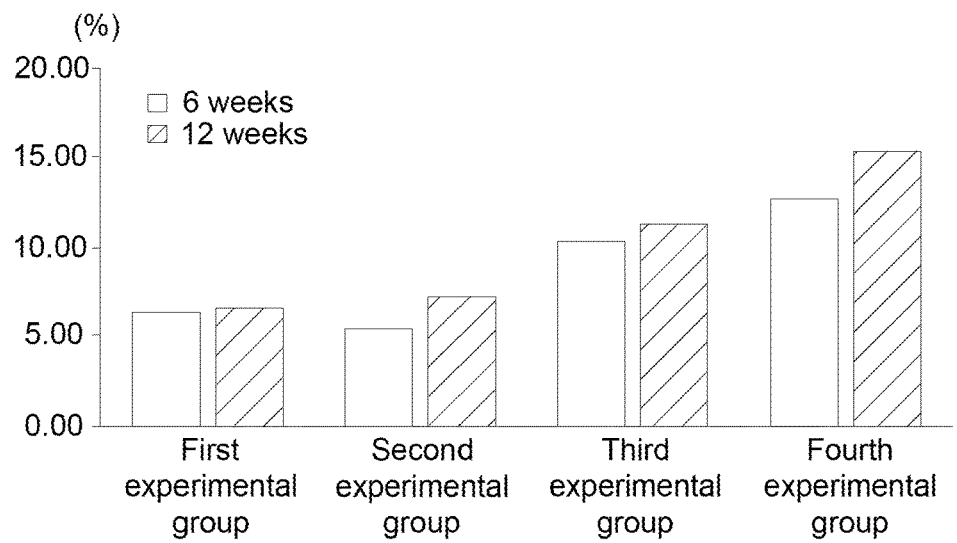
FIG. 11 is the result of measuring the bone volume of the control group and the first to fourth experimental groups in the animal experiment.

FIG. 11 is the result of measuring the bone volume of the control group and the first to fourth experimental groups in the animal experiment. It should be noted that the scattering effects of the material is too strong so that the bone volume of the control group (commercially available bone screw) may not be observed and could not be shown in FIG. 11. As shown in FIG. 11, the bone volumes of the third experimental group and the fourth experimental group are larger than the bone volumes of the first experimental group and the second experimental group.

Further, the bone volumes in the groups with growth factor BMP-2 (the second and fourth experimental groups) are obviously increased after twelve weeks than after six weeks. However, the bone volumes in the groups without growth factor BMP-2 (the first and third experimental groups) are not obviously increased after twelve weeks than after six weeks. As such, the bionic fixing apparatus in the embodiment according to the disclosure may have the ability of adding growth factor BMP-2. In particular, the bionic fixing apparatus in the first embodiment adding growth factor BMP-2 may be observed to have the most obvious increase of bone volume (but it may not reach a statistically significant difference).

It should be noted that although adding growth factors may help to bone growing, the growth factor itself is still doubted about the impact of the organism. For example, it is still unable to rule out the possibility that growth factors may cause biological cell disease or even cancer. Compared the result of measurement in the first experimental group with that in the second experimental group (or compared the result of measurement in the third experimental group with that in the fourth experimental group), it is shown that the increase of the bone volume after adding the growth factors may not reach a statistically significant difference. That is, the growth and combination of the organism tissues (such as bones) may be enhanced by using the bionic fixing apparatus in the embodiment according to the disclosure, and there is no need to add growth factors.

The mechanical test uses Mechanical Testing and Simulation (MTS) test system for testing. First, the samples are fixed into the South Asian PVC W200 water pipes (diameter 21.6 cm) by gypsum (gypsum:water=8:2) for one day. After the gypsum is cured, glass-reinforced plastics is stuffed in the tail of the bone screws, and a short (about 5 mm) hex wrench truncated fragments is enclosed to reinforce the strength of the bone screws. The sample connecting to the attached pipes mold is placed on the testing platform, and grippers are provided on the tail of the bone screws. The bone screws are locked until they could not be loosened (could not lock completely until the bone screws are unable to rotate, because the bone screws may be deformed). The grippers are suspended on the testing platform. The bone screws are pulled to completely release (the bone screws are loosened form the sample or the grippers are loosened from the bone screws) at 5 mm/min rate, and the experiment is finished.

Figure 12:
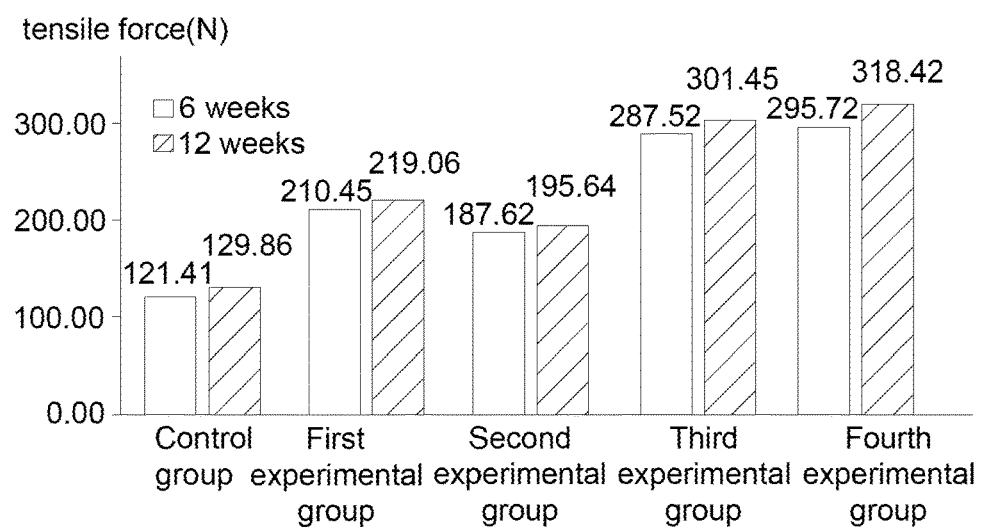
FIG. 12 is the result of mechanical test in the control group and the first to fourth experimental groups.

FIG. 12 is the result of mechanical test in the control group and the first to fourth experimental groups. As shown in FIG. 12, the apparatus in the control group is pulled out more easily, and only 120 N of the strength is required to loosen the apparatus. The apparatuses in the first and second experimental groups have higher mechanical strength (about 190 N) compared with the apparatus in the control group.

It is unfortunate that although the apparatuses in the third and fourth experiment have higher mechanical strength (about 300 N), the strength of the material itself could not be maintain during the experiment, such that the deformation is generated and the grippers is loosened. Therefore, the complete results of the experiment may not be achieved.

According to the embodiments and the experiments above, the bionic fixing apparatus in the embodiment of the disclosure may have better biocompatibility and mechanical strength compared with the conventional fixing apparatus such as bone screws. Further, various micro-structures in the embodiments mentioned above may be manufactured by an additive manufacturing process. The micro-structures may maintain the mechanical strength of the implants and enhance the growth and combination of the organism tissues.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A bionic fixing apparatus, comprising:
   a flexible portion having a plurality of diamond-shaped pores, wherein a pore size of each diamond-shaped pore is between 50 μm to 500 μm, and the diamond-shaped pores of the flexible portion are arranged in a grid array structure with a plurality of meshes, wherein each diamond-shaped mesh of the grid array structure is a smallest pore unit and has:
   two first included angles arranged along a force-receiving direction of the bionic fixing apparatus, wherein the force-receiving direction of the bionic fixing apparatus is along a longitudinal axis of the flexible portion; and
   two second included angles arranged along a direction perpendicular to the force-receiving direction of the bionic fixing apparatus, and each of the second included angles is smaller than 90 degrees to increase the compressive strength of the bionic fixing apparatus when a force is applied on the bionic fixing apparatus; and
   a supporting element disposed in the flexible portion, wherein the supporting element comprises a plurality of strip structures parallel to each other formed with the flexible portion in one-piece and disposed along the force-receiving direction of the bionic fixing apparatus.

2. The bionic fixing apparatus according to claim 1, further comprising:
   a rigid portion connected with the flexible portion, wherein the rigid portion and the flexible portion are one-piece formed.

3. The bionic fixing apparatus according to claim 1, wherein the pore size of each pore is between 50 μm to 200 μm.

4. The bionic fixing apparatus according to claim 3, wherein a porosity of the bionic fixing apparatus is between 0.17 and 0.36.

5. The bionic fixing apparatus according to claim 1, wherein the pore size of each pore is between 300 μm to 500 μm.

6. The bionic fixing apparatus according to claim 5, wherein a porosity of the bionic fixing apparatus is between 0.31 and 0.55.

7. The bionic fixing apparatus according to claim 1, wherein a material of the bionic fixing apparatus comprises metals, alloys, ceramics or polymeric biomaterials.

8. The bionic fixing apparatus according to claim 1, further comprising:
   a thread portion surrounding the flexible portion, wherein the thread portion and the flexible portion are one-piece formed.

9. The bionic fixing apparatus according to claim 1, wherein the bionic fixing apparatus is a hollow structure.

\* \* \* \* \*